United States Patent
Masuda

(10) Patent No.: US 10,055,841 B2
(45) Date of Patent: Aug. 21, 2018

(54) ULTRASONIC IMAGE APPARATUS, CONTROL DEVICE FOR ULTRASONIC IMAGE APPARATUS, AND ULTRASONIC IMAGE FORMING METHOD

(71) Applicant: SEIKO EPSON CORPORATION, Tokyo (JP)

(72) Inventor: Hiroyuki Masuda, Chino (JP)

(73) Assignee: SEIKO EPSON CORPORATION, Tokyo (JP)

( * ) Notice: Subject to any disclaimer, the term of this patent is extended or adjusted under 35 U.S.C. 154(b) by 24 days.

(21) Appl. No.: 15/296,582

(22) Filed: Oct. 18, 2016

(65) Prior Publication Data

US 2017/0124703 A1    May 4, 2017

(30) Foreign Application Priority Data

Nov. 2, 2015 (JP) ................................. 2015-215649

(51) Int. Cl.
*G06K 9/00* (2006.01)
*G06T 7/00* (2017.01)

(52) U.S. Cl.
CPC .. *G06T 7/0012* (2013.01); *G06T 2207/10132* (2013.01)

(58) Field of Classification Search
CPC .................................................. G06T 7/0012
USPC ....................................................... 382/128
See application file for complete search history.

(56) References Cited

U.S. PATENT DOCUMENTS

| 2009/0241673 A1* | 10/2009 | Kondo | G01N 29/0672 73/625 |
| 2010/0242610 A1* | 9/2010 | Karasawa | G01S 7/52085 73/597 |
| 2012/0212618 A1* | 8/2012 | Park | G01S 15/8977 348/163 |
| 2012/0269408 A1 | 10/2012 | Kim et al. | |
| 2012/0271144 A1 | 10/2012 | Kim et al. | |

FOREIGN PATENT DOCUMENTS

JP    2012-223584 A    11/2012
JP    2012-228513 A    11/2012

OTHER PUBLICATIONS

Austeng, Andreas et al., "Coherent Plane-Wave Compounding and Minimum Variance Beamforming", 2011 IEEE International Ultrasonics Symposium Proceedings, 2011, pp. 2448-2451.
Kraglund Holfort, Iben et al., "Adaptive Receive and Transmit Apodization for Synthetic Aperture Ultrasound Imaging", 2009 IEEE International Ultrasonics Symposium (IUS), 2009, pp. 1-4.

* cited by examiner

*Primary Examiner* — Raj Chakraborty
(74) *Attorney, Agent, or Firm* — Oliff PLC

(57) ABSTRACT

A signal synthesizing unit performs aperture synthesis of output signals from conversion element groups which are arranged in a matrix and convert ultrasonic waves into electric signals, and sequentially outputs a first image signal, for every transmission of the ultrasonic waves. A signal addition unit adds the first image signals output from the signal synthesizing unit together for each group so as to output a second image signal. An adaptive signal processing unit calculates an adaptive weight on the basis of the second image signal, and synthesizes the second image signals with each other.

18 Claims, 13 Drawing Sheets

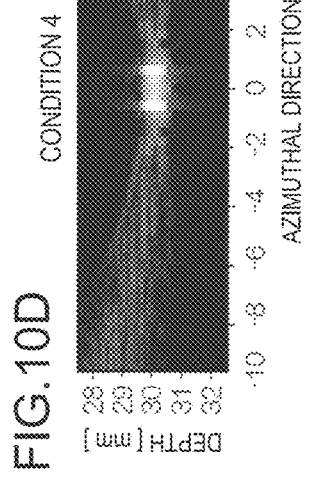
FIG.10A CONDITION 1
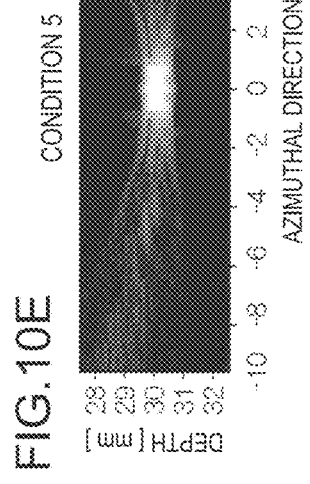
FIG.10B CONDITION 2
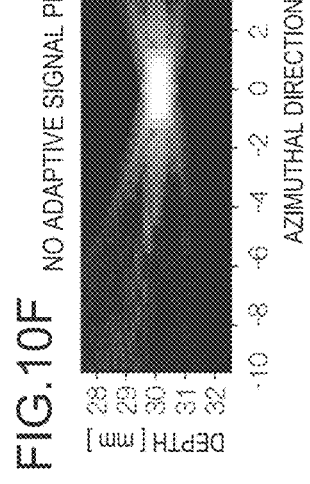
FIG.10C CONDITION 3
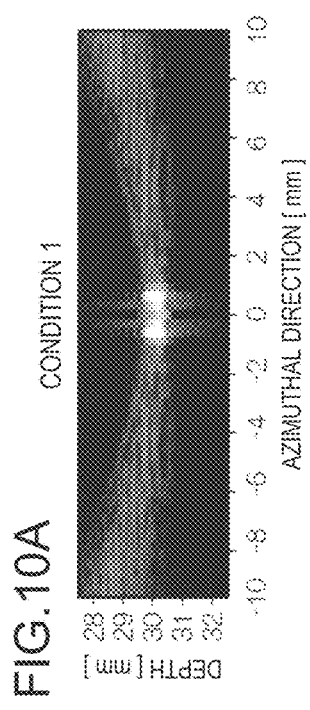
FIG.10D CONDITION 4
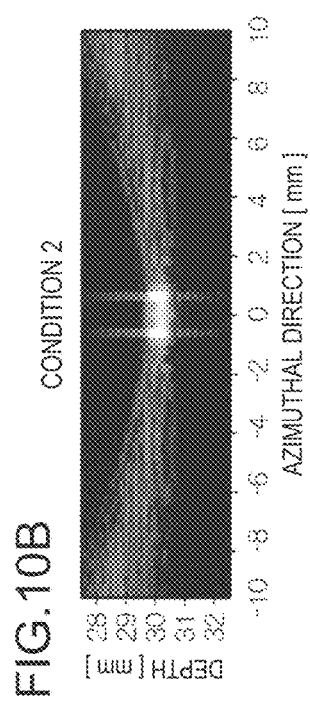
FIG.10E CONDITION 5
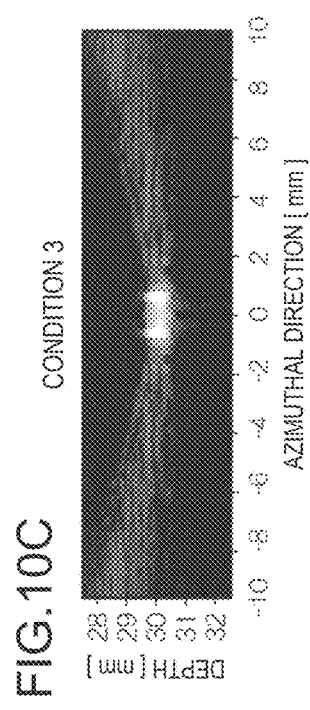
FIG.10F NO ADAPTIVE SIGNAL PROCESS

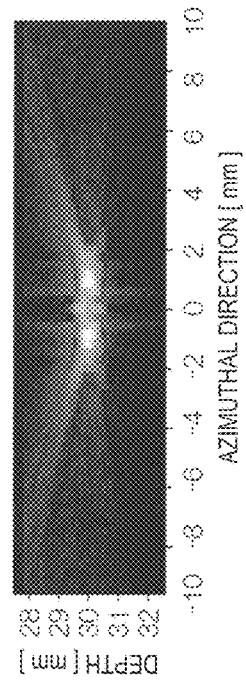
FIG.12A CONDITION 1
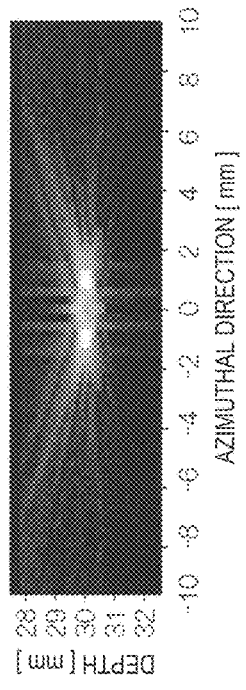
FIG.12B CONDITION 2
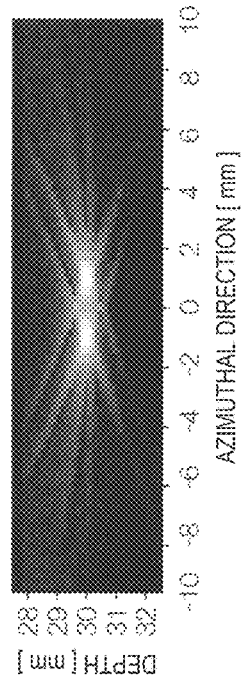
FIG.12C CONDITION 3
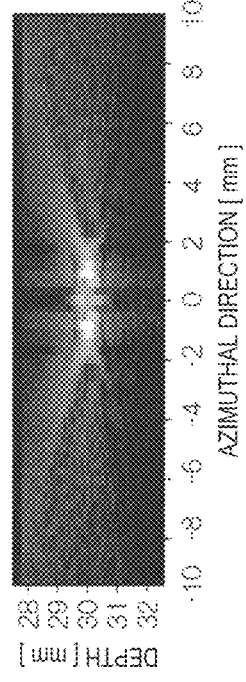
FIG.12D CONDITION 4
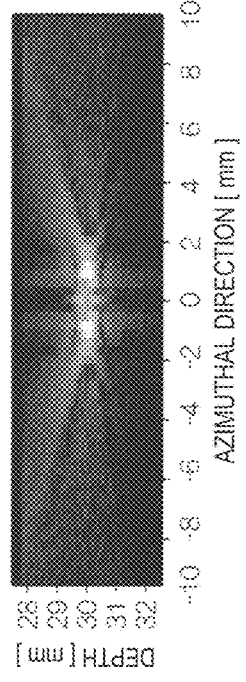
FIG.12E CONDITION 5
FIG.12F NO ADAPTIVE SIGNAL PROCESS

ULTRASONIC IMAGE APPARATUS, CONTROL DEVICE FOR ULTRASONIC IMAGE APPARATUS, AND ULTRASONIC IMAGE FORMING METHOD

BACKGROUND

1. Technical Field

The present invention relates to an ultrasonic image apparatus, a control device for the ultrasonic image apparatus, an ultrasonic image forming method, and the like.

2. Related Art

JP-A-2012-223584 discloses an adaptive beamforming process. A low resolution image is formed whenever ultrasonic waves are transmitted. A high resolution image is formed through synthesis using a plurality of low resolution images. An adaptive beamforming process is used to form the low resolution images. In the adaptive beamforming process, an adaptive beamforming coefficient which is used in common for the plurality of low resolution images is calculated. Therefore, a scale of calculation processing is considerably reduced compared with a case where an adaptive beamforming coefficient is calculated separately for each low resolution image.

However, in the adaptive beamforming, a measurement target object is narrowed down to one object. If a transmission condition such as a transmission element (position) or shift of a transmission angle differs, an adaptive beamforming coefficient also changes. Therefore, in a case where a common adaptive beamforming coefficient is used for a plurality of low resolution signals in which propagation paths of ultrasonic waves are different from each other, image quality deteriorates.

SUMMARY

An advantage of some aspects of the invention is to provide a control device for an ultrasonic image apparatus which can maintain favorable image quality while performing a synthesizing process based on an adaptive weight at a high speed.

(1) An aspect of the invention relates to a control device for an ultrasonic image apparatus including a signal synthesizing unit that performs aperture synthesis of output signals from conversion element groups which are arranged in a matrix and convert ultrasonic waves into electric signals, and that sequentially outputs a first image signal, for every transmission of the ultrasonic waves; a signal addition unit that adds the first image signals output from the signal synthesizing unit together for each group so as to output a second image signal; and an adaptive signal processing unit that calculates an adaptive weight on the basis of the second image signal, and synthesizes the second image signals with each other.

When the second image signals are synthesized with each other, an adaptive weight is calculated for each second image signal. A matrix calculation is performed during weighting. When the first image signal is added for each group in order to generate the second image signal, a scale of matrix calculation is reduced by the third power of the decrease in the number of signals compared with a case where an adaptive weight is individually calculated from the first image signal. In the above-described manner, the calculation scale is considerably reduced. A synthesis process based on the adaptive weight is performed at a high speed. In addition, favorable image quality can be maintained.

(2) The control device for an ultrasonic image apparatus may further include a transmission unit that outputs a transmission signal to a conversion element selected from the conversion element groups for every the transmission. Ultrasonic waves output from the conversion element groups are switched for every transmission, and thus a transmission position or a transmission angle can be changed. In the above-described manner, ultrasonic waves appropriate for synthesis of images can be transmitted from the conversion element groups.

(3) When S1 conversion elements which do not overlap each other among M conversion elements forming a column are sequentially driven, the number L of first image signals may be specified for each group according to the number K of transmissions and the number N of groups on the basis of the following equations:

$$K = \frac{M}{S1}$$

$$L = \left\lceil \frac{K}{N} \right\rceil \text{ or } \left\lfloor \frac{K}{N} \right\rfloor$$

provided that $$K = \left\lceil \frac{K}{N} \right\rceil \times K \bmod N + \left\lfloor \frac{K}{N} \right\rfloor \times (N - K \bmod N).$$

In the above-described manner, the number L of first image signals included in each group is restricted. A reduction in a resolution or a reduction in an adaptive signal processing effect due to grouping is prevented. M conversion elements may be arranged in a plurality of rows. In this case, the n-th S1 conversion elements in each column may be used in one transmission.

(4) When S1 conversion elements which are deviated by S2 among M conversion elements forming a column are sequentially driven, the number L of first image signals may be specified for each group according to the number K of transmissions and the number N of groups on the basis of the following equations:

$$K = \frac{M - S2}{S1 - S2}$$

$$L = \left\lceil \frac{K}{N} \right\rceil \text{ or } \left\lfloor \frac{K}{N} \right\rfloor$$

provided that $$K = \left\lceil \frac{K}{N} \right\rceil \times K \bmod N + \left\lfloor \frac{K}{N} \right\rfloor \times (N - K \bmod N).$$

In the above-described manner, the number L of first image signals included in each group is restricted. A reduction in a resolution or a reduction in an adaptive signal processing effect due to grouping is prevented. M conversion elements may be arranged in a plurality of rows. In this case, the n-th S1 conversion elements in each column may be used in one transmission.

(5) In a case where the transmission signal defines K output patterns forming a planar wave, a spread wave, or a converged wave in the conversion element groups, the number L of first image signals may be specified for each group according to the number K of transmissions and the number N of groups on the basis of the following equation:

$$L = \left\lceil \frac{K}{N} \right\rceil \text{ or } \left\lfloor \frac{K}{N} \right\rfloor$$

provided that $$K = \left\lceil \frac{K}{N} \right\rceil \times K \bmod N + \left\lfloor \frac{K}{N} \right\rfloor \times (N - K \bmod N).$$

In the above-described manner, the number L of first image signals included in each group is restricted. A reduction in a resolution or a reduction in an adaptive signal processing effect due to grouping is prevented.

(6) The number N of groups may be two or larger. An adaptive weight can be accurately calculated.

(7) The control device for an ultrasonic image apparatus may further include an input unit that is connected to an input device and inputs the number N of groups. The number of groups can be changed by operating the input device. It is possible to change the image quality of the second image signal according to the changing of the number of groups.

(8) The control device for an ultrasonic image apparatus may further include a setting unit that sets the number N of groups on the basis of an input value for specifying a resolution of the second image signal. A correlation is established between resolution of the second image signal and the number N of groups. In the conversion elements of a fixed number, if the number N of groups is reduced, a resolution of the second image signal is also reduced. A resolution mode may be set for each input value.

(9) The signal addition unit may add values of the first image signals together for each coordinate point. In the above-described manner, the signal values can be added together for each coordinate point regardless of the number of first image signals included in each group. Even if the number of signals differs for each group, an adaptive weight in the subsequent stage can be set on the basis of the number of signals. Even if the number of signals differs for each group, favorable image quality can be maintained.

(10) The control device for an ultrasonic image apparatus may be incorporated into, for example, an ultrasonic image apparatus, so as to be used. In this case, the ultrasonic image apparatus may include an apparatus main body that includes the control device for an ultrasonic image apparatus; and a probe that is connected to the apparatus main body and supports the conversion element groups.

(11) Another aspect of the invention relates to an ultrasonic image forming method including a procedure of performing aperture synthesis of output signals from conversion element groups which are arranged in a matrix and converting ultrasonic waves into electric signals, and sequentially outputting a first image signal, for every transmission of the ultrasonic waves; a procedure of adding the first image signals together for each group so as to output a second image signal; and a procedure of calculating an adaptive weight on the basis of the second image signal, and synthesizing the second image signals with each other.

BRIEF DESCRIPTION OF THE DRAWINGS

The invention will be described with reference to the accompanying drawings, wherein like numbers reference like elements.

FIGS. 10A to 10F are pictures illustrating ultrasonic images obtained through simulation.

FIGS. 12A to 12F are pictures illustrating ultrasonic images obtained through simulation.

DESCRIPTION OF EXEMPLARY EMBODIMENTS

Hereinafter, an embodiment of the invention will be described with reference to the drawings. The embodiments described below are not intended to improperly limit the content of the invention disclosed in the appended claims, and all constituent elements described below are not essential constituent elements of the invention.

(1) Entire Configuration of Ultrasonic Diagnosis Apparatus

Figure 1:
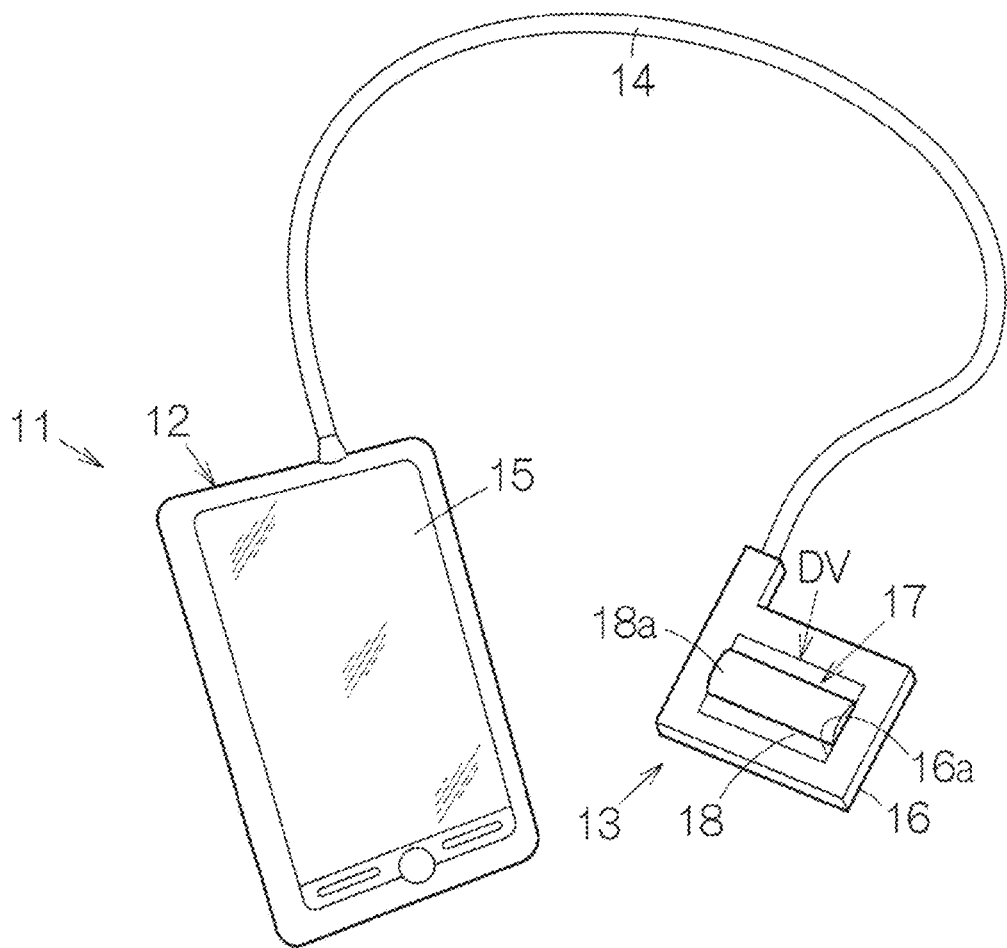
FIG. 1 is a schematic diagram illustrating a configuration of an ultrasonic diagnosis apparatus.

FIG. 1 schematically illustrates one specific example of an electronic apparatus according to an embodiment of the invention, that is, a configuration of an ultrasonic diagnosis apparatus (ultrasonic image apparatus) 11. The ultrasonic diagnosis apparatus 11 includes an apparatus terminal (apparatus main body) 12 and an ultrasonic probe (probe) 13. The apparatus terminal 12 and the ultrasonic probe 13 are connected to each other via a cable 14. The apparatus terminal 12 and the ultrasonic probe 13 transmit and receive electric signals therebetween via the cable 14. A display panel (display device) 15 is incorporated into the apparatus terminal 12. A screen of the display panel 15 is exposed to a surface of the apparatus terminal 12. The apparatus terminal 12 generates an image on the basis of ultrasonic waves detected by the ultrasonic probe 13. A detection result generated as the image is displayed on the screen of the display panel 15.

The ultrasonic probe 13 has a casing 16. An ultrasonic device unit DV is accommodated in the casing 16. The ultrasonic device unit DV includes an ultrasonic device 17. The ultrasonic device 17 is provided with an acoustic lens 18. An outer surface of the acoustic lens 18 is a partial cylindrical surface 18a. The acoustic lens 18 is made of, for example, silicon resin. The acoustic lens 18 has acoustic impedance close to acoustic impedance of a living body. A window hole 16a is defined in the casing 16. The acoustic lens 18 is disposed in the window hole 16a. The outer surface of the acoustic lens 18 is exposed to the surface of the casing 16. The ultrasonic device 17 outputs ultrasonic waves from a surface thereof, and receives reflected waves of the ultrasonic waves. The ultrasonic diagnosis apparatus 11 or the ultrasonic probe 13 may have a different structure.

(2) Configuration of Ultrasonic Device

Figure 2:
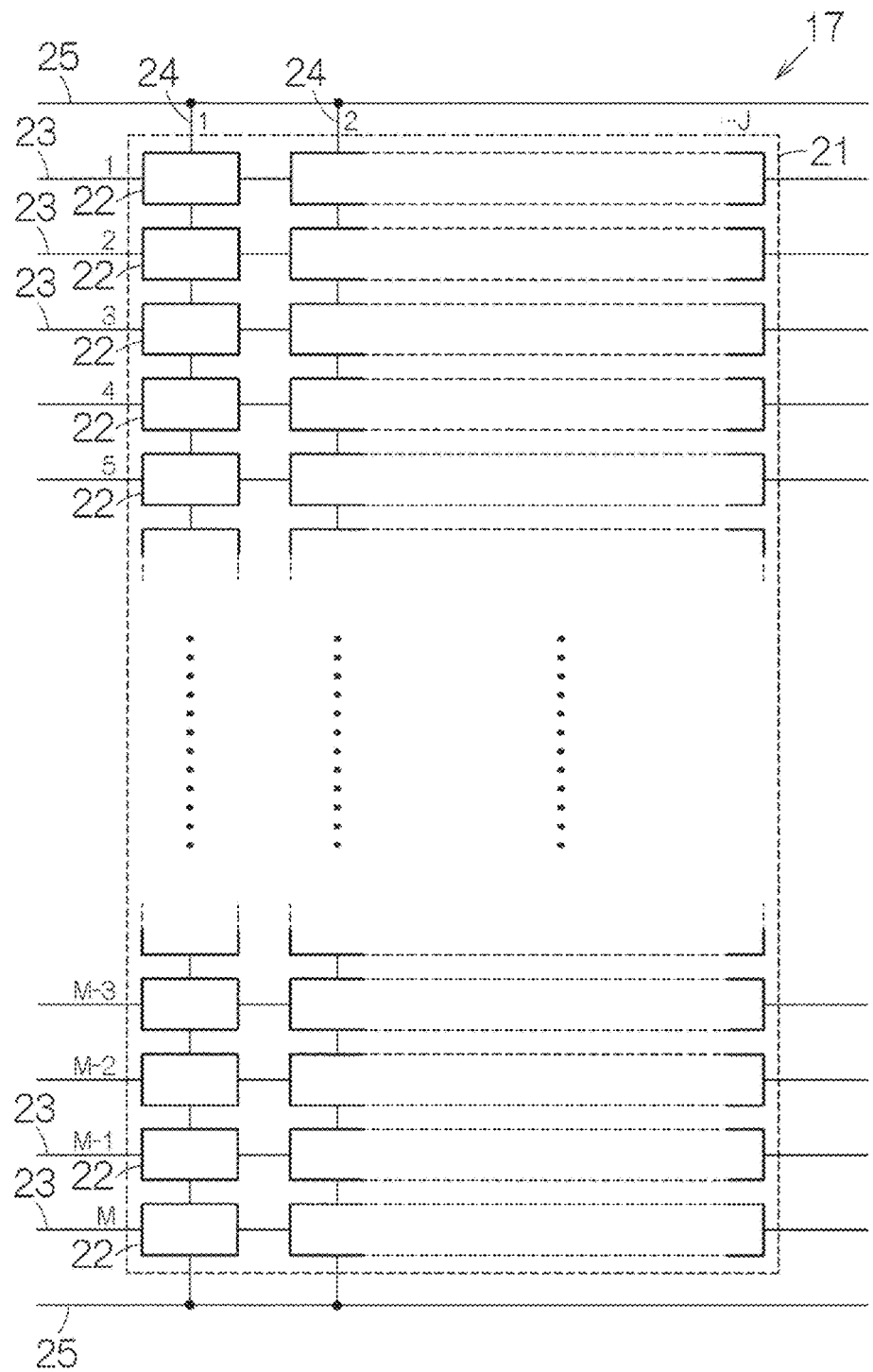
FIG. 2 is a plan view conceptually illustrating a configuration of an ultrasonic device.

FIG. 2 conceptually illustrates a configuration of the ultrasonic device 17. The ultrasonic device 17 includes an element array (conversion element group) 21. The element array 21 includes ultrasonic transducer elements (hereinafter, referred to as "conversion elements") 22 which are arranged in a matrix. Each of the conversion elements 22 receives ultrasonic waves and converts the ultrasonic waves into an electric signal. Each of the conversion elements 22 can transmit ultrasonic waves in response to the supply of an electric signal. In the element array 21, the conversion elements 22 are arranged in M rows and J columns. M conversion elements 22 are linearly arranged in each column. Here, the element array 21 is formed of the conversion elements 22 of 64 rows and 8 columns. However, the number of rows may be set to, for example, 128 or 256, and the number of columns may be set to, for example, about 10 to 15.

For example, a signal electrode line 23 is formed for each row of the conversion elements 22. The signal electrode line 23 connects the conversion elements 22 to each other for each row. A single signal electrode line 23 is connection in common to the conversion elements 22 in a plurality of rows. A common electrode line 24 is formed for each column of the conversion elements 22. The common electrode line 24 is connected to lead wires 25 at both ends thereof, for example. In the above-described manner, all of the conversion elements 22 are connected to the lead wires 25. Electric signals are transmitted and received through each signal electrode line 23.

Figure 3:
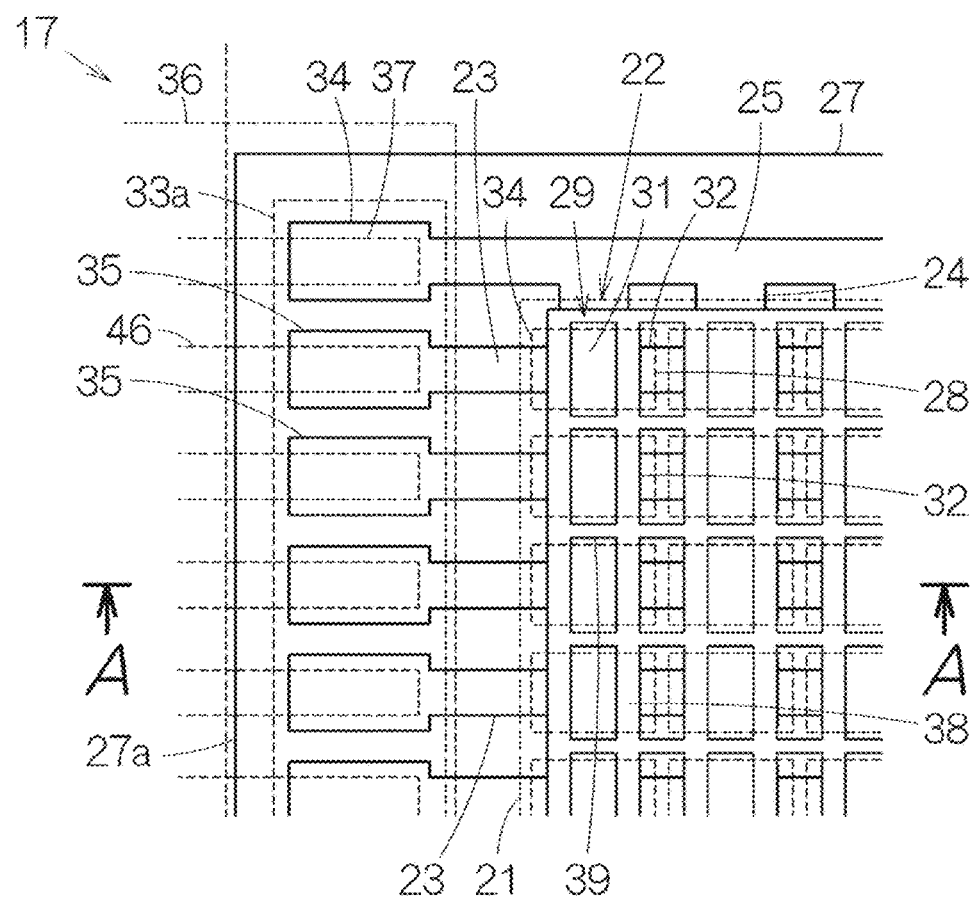
FIG. 3 is a partial plan view specifically illustrating a structure of the ultrasonic device.

FIG. 3 is more specifically illustrates a structure of the ultrasonic device 17. The ultrasonic device 17 is provided with a base 27. The conversion elements 22 are formed on the base 27. Each of the conversion elements 22 is provided with a vibration film 28. Details of the vibration film 28 will be described later. In FIG. 3, a contour of the vibration film 28 is illustrated by a dotted line in a plan view (a plan view in a thickness direction of the substrate) in a direction orthogonal to a surface of the vibration film 28. A piezoelectric element 29 is formed on the vibration film 28. In the piezoelectric element 29, as will be described later, a piezoelectric film (not illustrated) is interposed between an upper electrode 31 and a lower electrode 32. These are stacked in order. The ultrasonic device 17 is configured as a single ultrasonic transducer element chip.

The signal electrode lines 23, the common electrode lines 24, and the lead wires 25 are formed on a surface of the base 27. The signal electrode line 23 forms the lower electrode 32 in each of the conversion elements 22. The common electrode line 24 forms the upper electrode 31 in each of the conversion elements 22. For example, a laminate film of titanium (Ti), iridium (Ir), platinum (Pt), and titanium (Ti) may be used for the signal electrode line 23. The common electrode lines 24 and the lead wires 25 may be made of, for example, iridium (Ir). However, other conductive materials may be used for the signal electrode lines 23, the common electrode lines 24, and the lead wires 25.

A contour of the base 27 is divided into a pair of straight lines which are parallel to each other, and has a first side 27a and a second side (not illustrated) which oppose each other. A first terminal array 33a is disposed in a line between the first side 27a and the contour of the element array 21. A second terminal array (not illustrated) is disposed in a line between the second side and the contour of the element array 21. The first terminal array 33a is formed of a pair of upper electrode terminals 34 and a plurality of lower electrode terminals 35. The upper electrode terminals 34 are connected to the lead wires 25. The lower electrode terminals 35 are connected to the signal electrode lines 23. Similarly, a second terminal array (not illustrated) may be disposed in a line between the second side and the contour of the element array 21.

The base 27 is connected to a flexible printed wiring board (hereinafter, referred to as a "wiring board") 36. The wiring board 36 covers the first terminal array 33a. Conductive lines, that is, signal lines 37 are formed to individually correspond to the upper electrode terminals 34 and the lower electrode terminals 35 are formed at one of the wiring board 36. The signal lines 37 individually face the upper electrode terminals 34 and the lower electrode terminals 35 so as to be individually joined thereto.

An electrode isolation film 38 is disposed on the vibration film 28 in parallel to the common electrode line 24. The electrode isolation film 38 extends in a strip shape in the longitudinal direction of the common electrode line 24. The electrode isolation film 38 has insulating property and moisture resistance. The electrode isolation film 38 is made of, for example, a moisture resistant insulating material such as alumina ($Al_2O_3$) or silicon oxide ($SiO_2$). The electrode isolation films 38 are formed separately on both sides of the common electrode line 24 with the common electrode line 24 interposed therebetween. The common electrode line 24 intersects the signal electrode line 23 over the vibration film 28, and thus the electrode isolation film 38 crosses the signal electrode line 23 over the vibration film 28.

Insulating films 39 are formed in regions other than a region of the vibration films 28 on the base 27. Each of the insulating films 39 extends in the longitudinal direction of the signal electrode line 23. The insulating film 39 is disposed in parallel to the signal electrode line 23 in regions other than the vibration film 28. The insulating film 39 is made of, for example, humidity resistant insulating material such as alumina or silicon oxide. The insulating film 39 crosses the common electrode line 24. The insulating film 39 is connected to the electrode isolation film 38.

Figure 4:
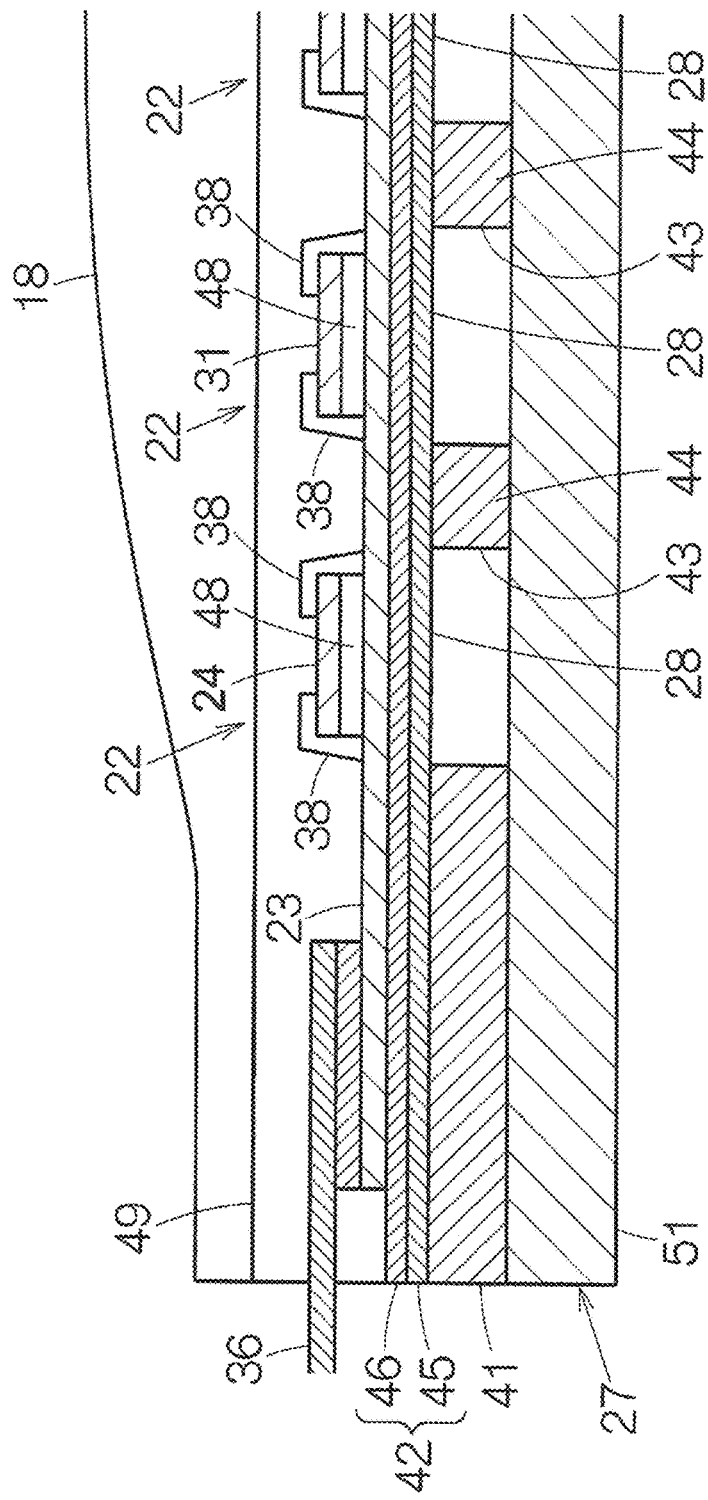
FIG. 4 is a partial sectional view taken along the line A-A in FIG. 3.

As illustrated in FIG. 4, the base 27 includes a substrate 41 and a flexible film 42. The flexible film 42 is formed on one surface of the substrate 41. An opening 43 is formed for each of the conversion elements 22 in the substrate 41. The openings 43 are arranged in a matrix in the substrate 41. A partition wall 44 is defined between two adjacent openings 43. The adjacent openings 43 are partitioned from each other by the partition wall 44.

The flexible film 42 is formed of a silicon oxide ($SiO_2$) layer 45 laminated on the surface of the substrate 41, and a zirconium oxide ($ZrO_2$) layer 46 laminated on a surface of the silicon oxide layer 45. The flexible film 42 is in contact with the openings 43. In this way, a part of the flexible film 42 forms the vibration film 28 so as to correspond to a contour of the opening 43. A film thickness of the silicon oxide layer 45 may be determined on the basis of a resonance frequency.

The signal electrode line 23, the piezoelectric film 48, and the common electrode line 24 are sequentially laminated on a surface of the vibration film 28. The piezoelectric film 48 may be made of, for example, lead zirconate titanate (PZT). Other piezoelectric materials may be used for the piezoelectric film 48. Here, the piezoelectric film 48 completely covers the surface of the signal electrode line 23 under the common electrode line 24. The signal electrode line 23 can be prevented from being short-circuited to the common electrode line 24 due to the working of the piezoelectric film 48. The surface of the piezoelectric film 48 is covered with the electrode isolation film 38.

An acoustic matching layer 49 is laminated on the surface of the base 27. The acoustic matching layer 49 covers the element array 21. A film thickness of the acoustic matching layer 49 is determined according to a resonance frequency of the vibration film 28. For example, a silicon resin film may be used for the acoustic matching layer 49. The acoustic lens 18 is disposed on the acoustic matching layer 49. The acoustic lens 18 is in close contact with the surface of the acoustic matching layer 49 on a rear plane of the partial cylindrical surface 18a. The acoustic lens 18 is adhered to the base 27 due to the working of the acoustic matching layer 49. A generatrix of the partial cylindrical surface 18a is arranged to be parallel to the signal electrode line 23. The curvature of the partial cylindrical surface 18a is determined according to a focal position of ultrasonic waves emitted from the conversion elements 22 of one row connected to a single signal electrode line 23.

The rear surface of the base 27 is coupled to a reinforcing plate 51 as a backing material. The reinforcing plate 51 is formed in a plate shape. The rear surface of the base 27 overlaps a front surface of the reinforcing plate 51. The front surface of the reinforcing plate 51 is joined to the rear surface of the base 27. In this joining, the reinforcing plate 51 may be adhered to the base 27 via an adhesive. The reinforcing plate 51 reinforces the rigidity of the base 27. The reinforcing plate 51 may be provided with, for example, a rigid base material. The base material may be made of, for example, a metal material such as 42 Alloy (iron-nickel alloy).

(3) Circuit Configuration of Ultrasonic Diagnosis Apparatus

Figure 5:
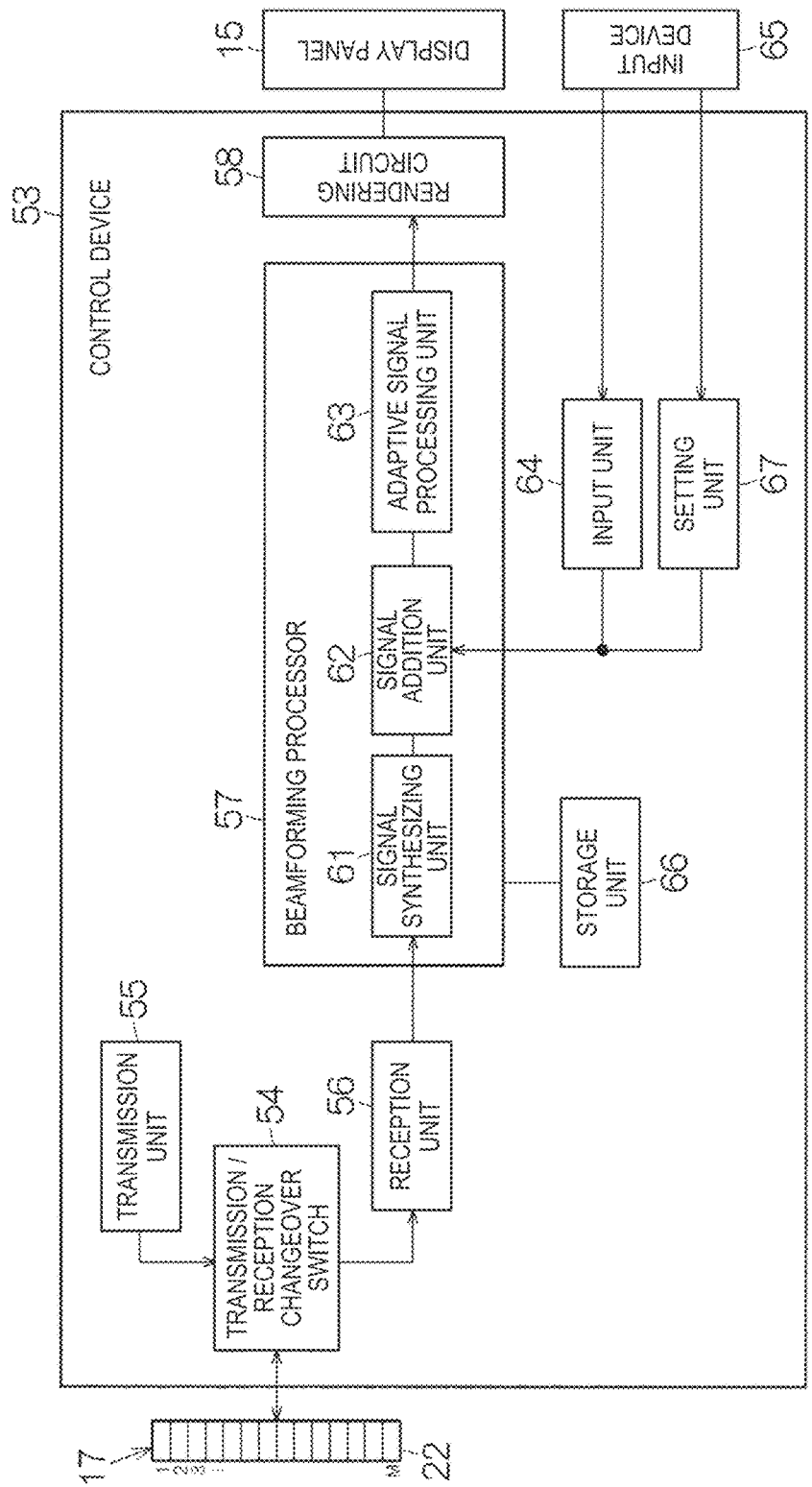
FIG. 5 is a block diagram schematically illustrating a circuit configuration of the ultrasonic diagnosis apparatus.

As illustrated in FIG. 5, the ultrasonic device 17 is connected to a control device 53. The control device 53 is incorporated into, for example, the apparatus terminal 12. The control device 53 is connected to the display panel 15. A video signal is supplied to the display panel 15 from the control device 53. An ultrasonic image or other information is displayed on the screen of the display panel 15 on the basis of the supplied video signal.

The control device 53 includes a transmission/reception changeover switch 54. The transmission/reception changeover switch 54 is connected to the signal electrode lines 23 of the ultrasonic device 17. The transmission/reception changeover switch 54 is connected to a transmission unit 55 and a reception unit 56. During transmission of ultrasonic waves, the transmission/reception changeover switch 54 connects the signal electrode lines 23 to the transmission unit 55. At this time, the reception unit 56 is disconnected from the transmission unit 55 and the signal electrode lines 23. During reception of ultrasonic waves, the transmission/reception changeover switch 54 connects the signal electrode lines 23 to the reception unit 56. At this time, the transmission unit 55 is disconnected from the reception unit 56 and the signal electrode lines 23.

The transmission unit 55 outputs a transmission signal to the conversion elements 22 selected from the element array 21 via the transmission/reception changeover switch 54 for every transmission. The transmission unit 55 may include, for example, a pulse generator and a delay circuit. The pulse generator outputs a pulse voltage. The pulse voltage is applied to the piezoelectric film 48 of the conversion element 22. The vibration film 28 is brought into ultrasonic vibration due to the supply of the pulse voltage. Thus, ultrasonic waves are emitted from the conversion element 22. The delay circuit may cause a time difference in application of voltages to the signal electrode lines 23. The time difference in the application determines a propagation direction of an ultrasonic wave output from the conversion element 22. It is possible to control a transmission direction of a planar wave by changing delay time.

The reception unit 56 receives a signal from the conversion element 22. Ultrasonic waves reflected from a measurement target bring the vibration film 28 of the conversion element 22 into ultrasonic vibration. A reception signal is output from the piezoelectric film 48 due to the ultrasonic vibration. The reception signal is stored in the reception unit 56. The reception unit 56 may be provided with, for example, a storage portion such as a memory or a hard disk drive (HDD).

The control device 53 includes a beamforming processor 57. The beamforming processor 57 is connected to the reception unit 56. The beamforming processor 57 generates rendering data of an ultrasonic image on the basis of a reception signal supplied from the reception unit 56.

The control device 53 includes a rendering circuit 58. The rendering circuit 58 is connected to the beamforming processor 57. The rendering circuit 58 is connected to the display panel 15. The rendering circuit 58 generates a drive signal on the basis of the rendering data generated by the beamforming processor 57. The drive signal is transmitted to the display panel 15. As a result, an image is displayed on the display panel 15.

The beamforming processor 57 includes a signal synthesizing unit 61. The signal synthesizing unit 61 is connected to the reception unit 56. The signal synthesizing unit 61 acquires M reception signals obtained through one transmission, from the reception unit 56. The signal synthesizing unit 61 performs aperture synthesis of M reception signals for every transmission of ultrasonic waves. The signal synthesizing unit 61 outputs a first image signal (low resolution signal) obtained through the aperture synthesis. During the aperture synthesis, the signal synthesizing unit 61 may perform phasing addition.

Figure 6:
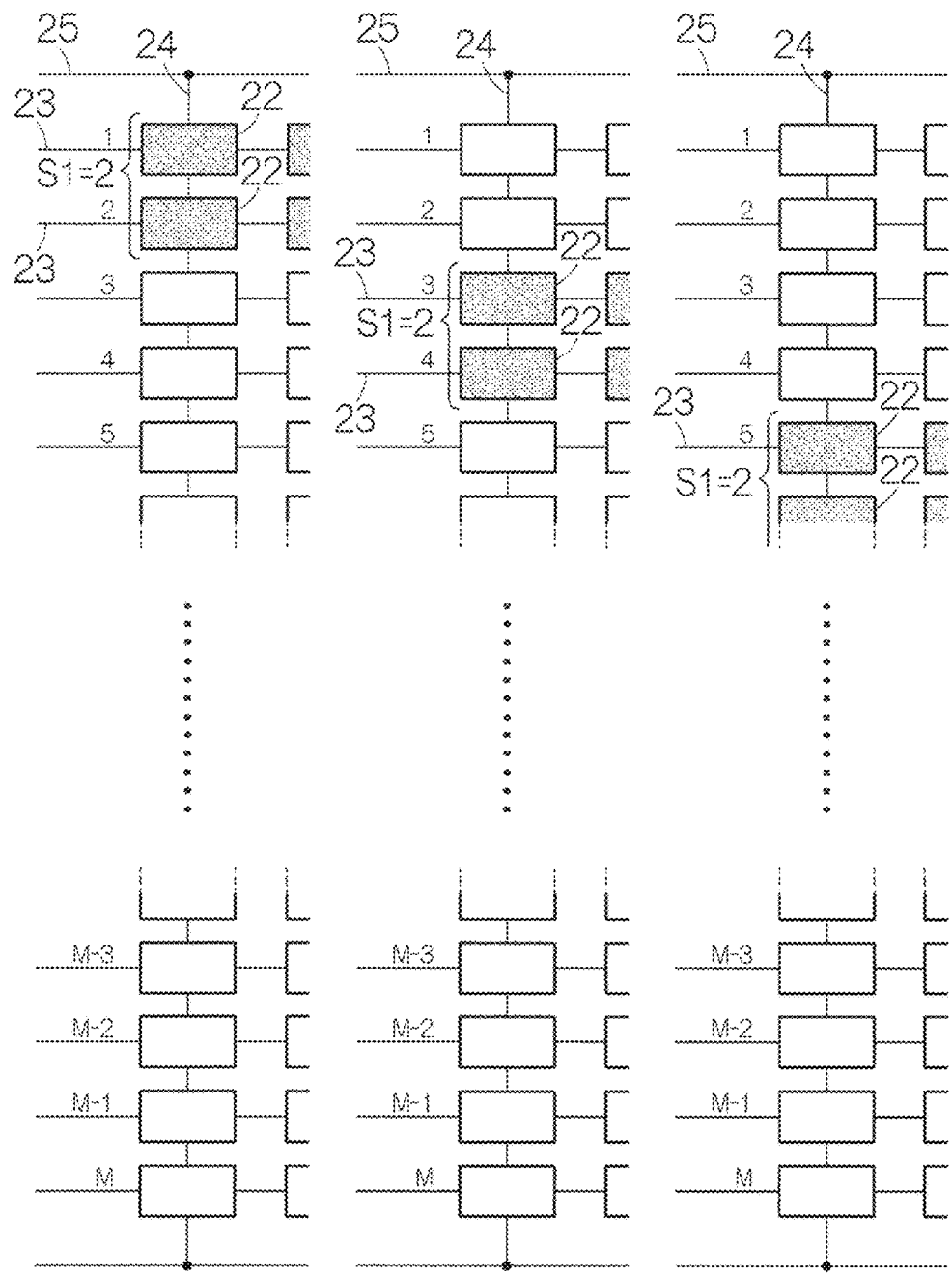
FIG. 6 is a plan view schematically illustrating a first transmission mode.

The beamforming processor 57 includes a signal addition unit 62. The signal addition unit 62 is connected to the signal synthesizing unit 61. The signal addition unit 62 adds first image signals output from the signal synthesizing unit 61 together for each group. As a result of the addition, the signal addition unit 62 outputs a second image signal for each group. During the addition of the first image signals, the signal addition unit 62 specifies the number K of transmissions and the number N of groups. The number K of transmissions is determined according to a transmission mode. For example, in a first transmission mode, S1 conversion elements 22 which do not overlap each other are driven among the M conversion elements 22 forming a column. In FIG. 6, ultrasonic waves are emitted from the conversion elements 22 of two (=S1) rows, and ultrasonic waves are emitted from the conversion elements 22 of the next two (=S1) rows deviated therefrom by two rows. In this case, an upper limit of the number L of first image signals is given by the following equations for each group according to the number K of transmissions and the number N of groups:

$$K = \frac{M}{S1}$$

$$L = \left\lceil \frac{K}{N} \right\rceil \text{ or } \left\lfloor \frac{K}{N} \right\rfloor$$

provided that $$K = \left\lceil \frac{K}{N} \right\rceil \times K \bmod N + \left\lfloor \frac{K}{N} \right\rfloor \times (N - K \bmod N).$$

Figure 7:
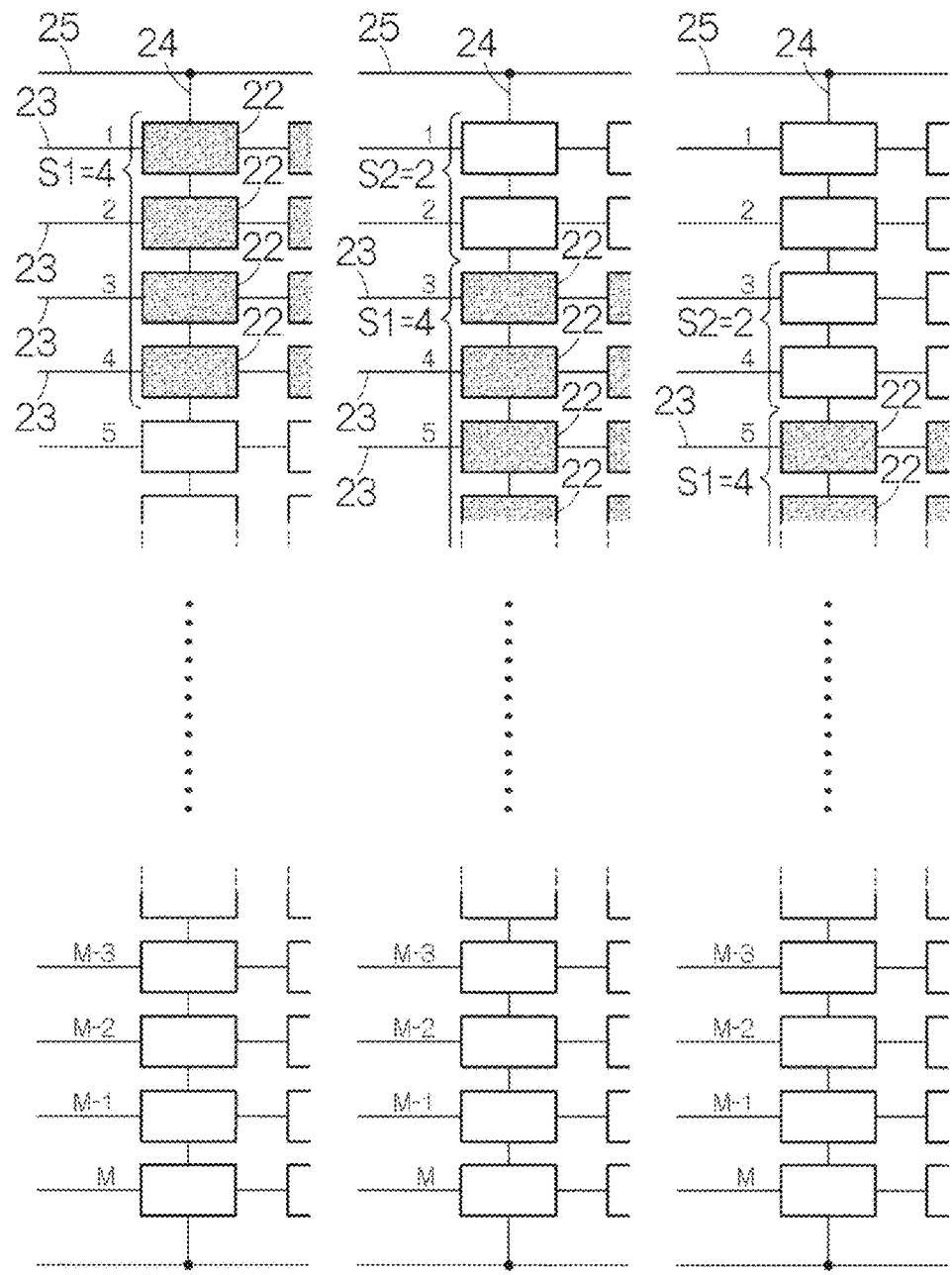
FIG. 7 is a plan view schematically illustrating a second transmission mode.
Figure 8:
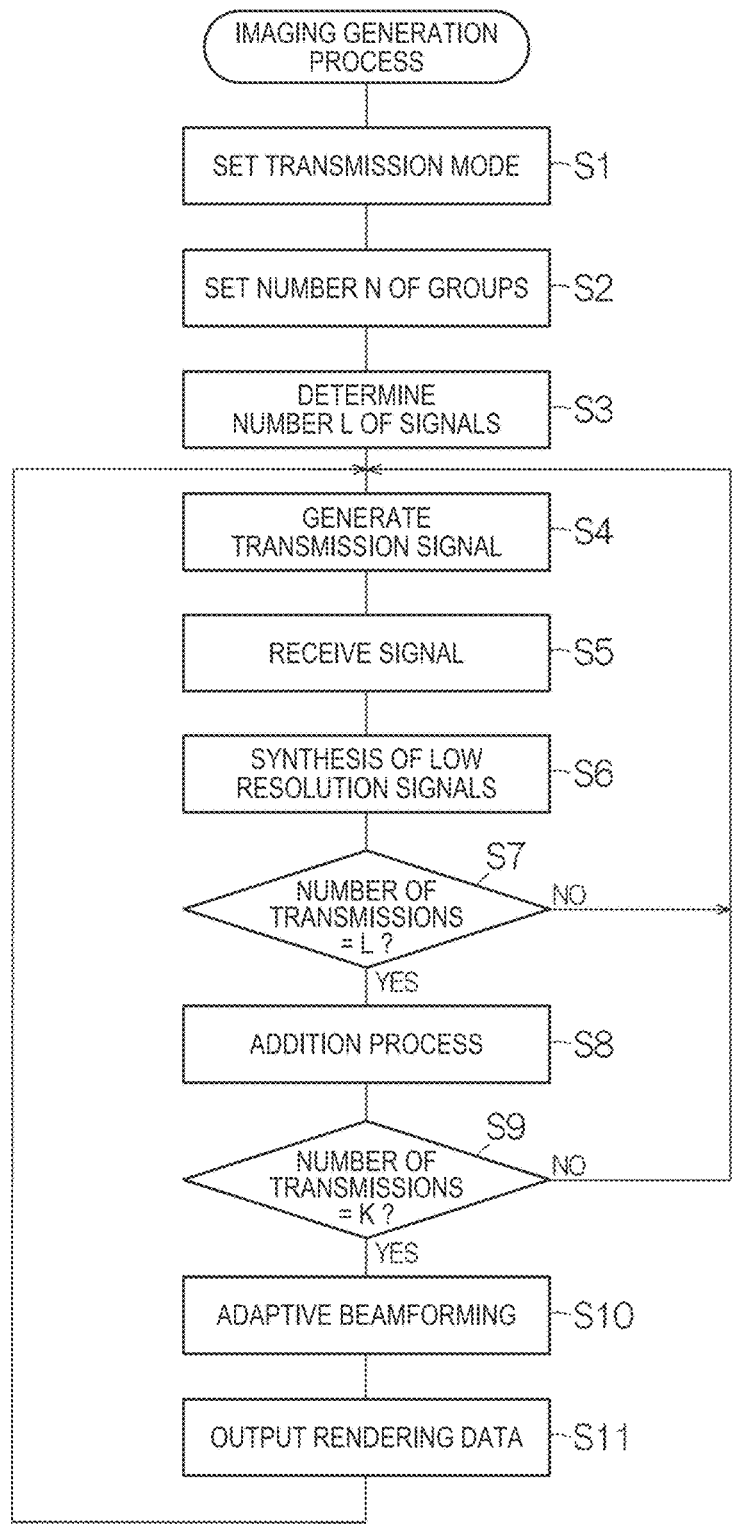
FIG. 8 is a flowchart schematically illustrating an operation of the ultrasonic diagnosis apparatus.

For example, in a second transmission mode, S1 conversion elements 22 are sequentially driven at the same time while being deviated by S2 among the M conversion elements 22 forming a column. In FIG. 7, ultrasonic waves are emitted from the conversion elements 22 of four (=S1) rows, and ultrasonic waves are emitted from the conversion elements 22 of the next four (=S1) rows deviated therefrom by two (=S2) rows. Compared with the case of FIG. 6, the resolution is maintained, and the intensity of ultrasonic waves can be increased. In this case, an upper limit of the number L of first image signals is given by the following equations for each group according to the number K of transmissions and the number N of groups:

$$K = \frac{M - S2}{S1 - S2}$$

$$L = \left\lceil \frac{K}{N} \right\rceil \text{ or } \left\lfloor \frac{K}{N} \right\rfloor$$

provided that $$K = \left\lceil \frac{K}{N} \right\rceil \times K \bmod N + \left\lfloor \frac{K}{N} \right\rfloor \times (N - K \bmod N).$$

For example, in a third transmission mode, K output patterns forming planar waves may be defined in the element array 21. A transmission direction may be changed for each output pattern by the above-described function of the delay circuit. In this case, the number L of first image signals is given by the following equation for each group according to the number K of transmissions and the number N of groups:

$$L = \left\lceil \frac{K}{N} \right\rceil \text{ or } \left\lfloor \frac{K}{N} \right\rfloor$$

provided that $$K = \left\lceil \frac{K}{N} \right\rceil \times K \bmod N + \left\lfloor \frac{K}{N} \right\rfloor \times (N - K \bmod N).$$

A spread wave or a converged wave may be used instead of a planar wave.

The beamforming processor 57 includes an adaptive signal processing unit 63. The adaptive signal processing unit 63 is connected to the signal addition unit 62. The adaptive signal processing unit 63 calculates an adaptive weight on the basis of the second image signal. Matrix calculation is performed in the calculation of an adaptive weight. The adaptive signal processing unit 63 synthesizes the second image signals according to a weight of each second image signal. As a result of the synthesis, rendering data (high resolution image) is output from the adaptive signal processing unit 63. A process using a covariance matrix, such as an MV method, a DCMP method, or MUSIC may be used to calculate a weighting factor.

The control device 53 includes an input unit 64. The input unit 64 is connected to the signal addition unit 62. The input unit 64 is connected to an input device 65. The number N of groups may be input to the input unit 64 by operating the input device 65. The input unit 64 supplies the number N of groups to the signal addition unit 62. The number N of groups may be held in a storage unit 66. As the input device 65, a keyboard, a mouse, a touch screen panel, and other devices may be used. The second image signal from the signal addition unit 62 may be preserved in the storage unit 66 prior to calculation of an adaptive weight. If the number N of groups is 2 or larger, an adaptive weight can be accurately calculated.

The control device 53 includes a setting unit 67. The setting unit 67 is connected to the signal addition unit 62. The setting unit 67 is connected to the input device 65. An input value for specifying a resolution of the second image signal may be input by using the input device 65. For example, a transmission mode may be selected by inputting such an input value. The input value which is input is supplied to the setting unit 67. The setting unit 67 may set the number N of groups according to the input value. The set number N of groups may be supplied to the signal addition unit 62. The setting unit 67 may acquire the number N of groups from the storage unit 66, for example, for each transmission mode.

(4) Operation of Ultrasonic Diagnosis Apparatus

Next, a description will be made of an operation of the ultrasonic diagnosis apparatus 11. The control device 53 sets a transmission mode in step S1. The first transmission mode, the second transmission mode, or the third transmission mode is specified. A set transmission mode may be input, for example, by operating the input device 65. Alternatively, a transmission mode may be set in each ultrasonic diagnosis apparatus 11 in advance according to an application of an ultrasonic image. A transmission mode in each ultrasonic diagnosis apparatus 11 may be fixed to any one of the transmission modes in advance. If the transmission mode is set, the number K of transmissions is determined in accordance with the number M of elements in one column.

In step S2, the control device 53 sets the number N of groups. The number N of groups may be input, for example, by operating the input device 65. The input unit 64 supplies a notification signal of the number N of groups to the signal addition unit 62. In the above-described way, the number N of groups can be changed by operating the input device 65. The quality of an ultrasonic image can be changed according to the change of the number N of groups. The number N of groups may be held in the signal addition unit 62 in advance for each individual ultrasonic diagnosis apparatus 11. In a case where a transmission mode is set by using the input device 65, the setting unit 67 sets the number N of groups on the basis of the set transmission mode. Each transmission mode indicates an input value for specifying a resolution of an ultrasonic image. A correlation is established between the number N of groups and the resolution. In the conversion elements 22 of a fixed number M, if the number N of groups is reduced, a resolution of an ultrasonic image is also reduced. A resolution may be set for each transmission mode.

In step S3, the signal addition unit 62 determines the number L of first image signals for each group according to the number N of groups. The number L of first image signals included in each group is restricted depending on the number K of transmissions and the number N of groups.

In step S4, the transmission unit 55 outputs a transmission signal to the conversion elements 22 selected from the element array 21 for every transmission. The conversion elements 22 are selected on the basis of the transmission mode. The conversion elements 22 are brought into ultrasonic vibration due to the supply of the transmission signal. Ultrasonic waves are emitted to a target object on the basis of the transmission mode. In the first transmission mode or the second transmission mode, ultrasonic waves are emitted from the conversion elements 22 of one row. In the third transmission mode, ultrasonic waves are emitted from the element array 21 at a specific angle. The element array 21 receives ultrasonic waves reflected from the target object.

In step S5, the reception unit 56 receives a signal for each signal electrode line 23. The received signal is temporarily stored. In step S6, the signal synthesizing unit 61 performs aperture synthesis of output signals from the element array 21. The first image signal (low resolution signal) is output from the signal synthesizing unit 61 as a result of the aperture synthesis. In step S7, the number L of first image signals is determined. The processing operations in steps S4 to S7 are repeatedly performed until the number of transmissions reaches the number L of signals. At this time, ultrasonic waves output from the element array are switched for every transmission. In the first transmission mode or the second transmission mode, a transmission position of an ultrasonic wave is changed. In the third transmission mode, a transmission angle of a planar wave is changed. In the above-described manner, ultrasonic waves appropriate for synthesis of images can be transmitted from the element array 21.

If the number of transmissions reaches the number L of signals in step S7, the signal addition unit 62 adds the first image signals together for each group in step S8. The signal addition unit 62 adds values of the first image signals together for each coordinate point. As a result of the addition, the second image signal is output from the signal addition unit 62. In step S9, the number of second image signals corresponding to the number N of groups is counted.

If the second image signals are all output in step S9, the adaptive signal processing unit 63 performs adaptive beamforming on the second image signals in step S10. An adaptive weight, that is, an adaptive beamforming coefficient is calculated during execution of the adaptive beamforming. The second image signals are synthesized by using the calculated adaptive beamforming coefficient. In the above-described way, a high resolution signal is generated. The high resolution signal specifies rendering data of a high resolution image. The rendering data is output from the adaptive signal processing unit 63. The rendering data is supplied to the rendering circuit 58 in step S9. The rendering circuit 58 generates a drive signal on the basis of the rendering data. The drive signal is transmitted to the display panel 15. As a result, an image of one frame is displayed on the display panel 15. The processing operation returns to step S4. A video is formed as a result of the operations in steps S4 to S11 being repeatedly performed.

The adaptive signal processing unit 63 calculates an adaptive weight for each second image signal when synthesizing the second image signals. Matrix calculation is performed during weighting. When the first image signal is added for each group in order to generate the second image signal, a scale of matrix calculation is reduced by the third power of the decrease in the number of signals compared with a case where an adaptive weight is individually calculated from the first image signal. In the above-described manner, the calculation scale is considerably reduced. A synthesis process based on the adaptive weight is performed at a high speed. In addition, favorable image quality can be maintained. Even in a case where a difference in a propagation path is great, if grouping is performed after a low resolution signal with a small difference in the propagation path is selected, a calculation amount can be reduced. On the other hand, in a case where a weighting factor is used in common for a plurality of low resolution signals, the weighting factor cannot be shared if a difference in a propagation path is great.

As described above, the number L of first image signals included in each group is restricted. A reduction in a resolution or a reduction in an adaptive signal processing effect due to grouping is prevented. In the element array 21, the conversion elements 22 are arranged in M rows. The S1 conversion elements 22 of an n-th row are used in one transmission.

The signal addition unit 62 adds values of the first image signals together for each coordinate point. In the above-described manner, the signal values can be added together for each coordinate point regardless of the number of first image signals included in each group. Even if the number of signals differs for each group, an adaptive weight in the subsequent stage can be set on the basis of the number of signals. Even if the number of signals differs for each group, favorable image quality can be maintained. However, in a case where the number of first image signals differs for each group, an output signal preferably has an addition average value. Then, a signal intensity difference between groups can be reduced as much as possible.

(5) Verification of Present Embodiment

Figure 9:
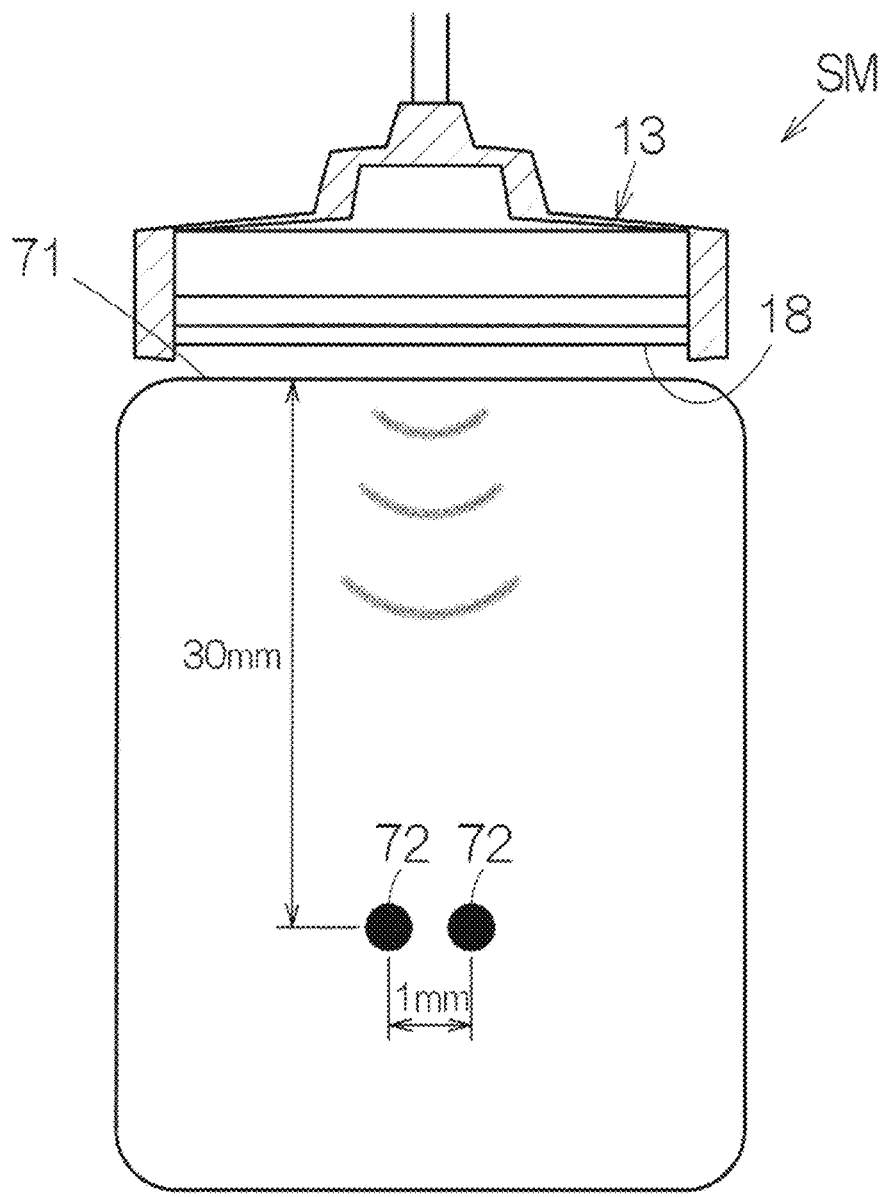
FIG. 9 is a conceptual diagram schematically illustrating a simulation model.
Figure 11:
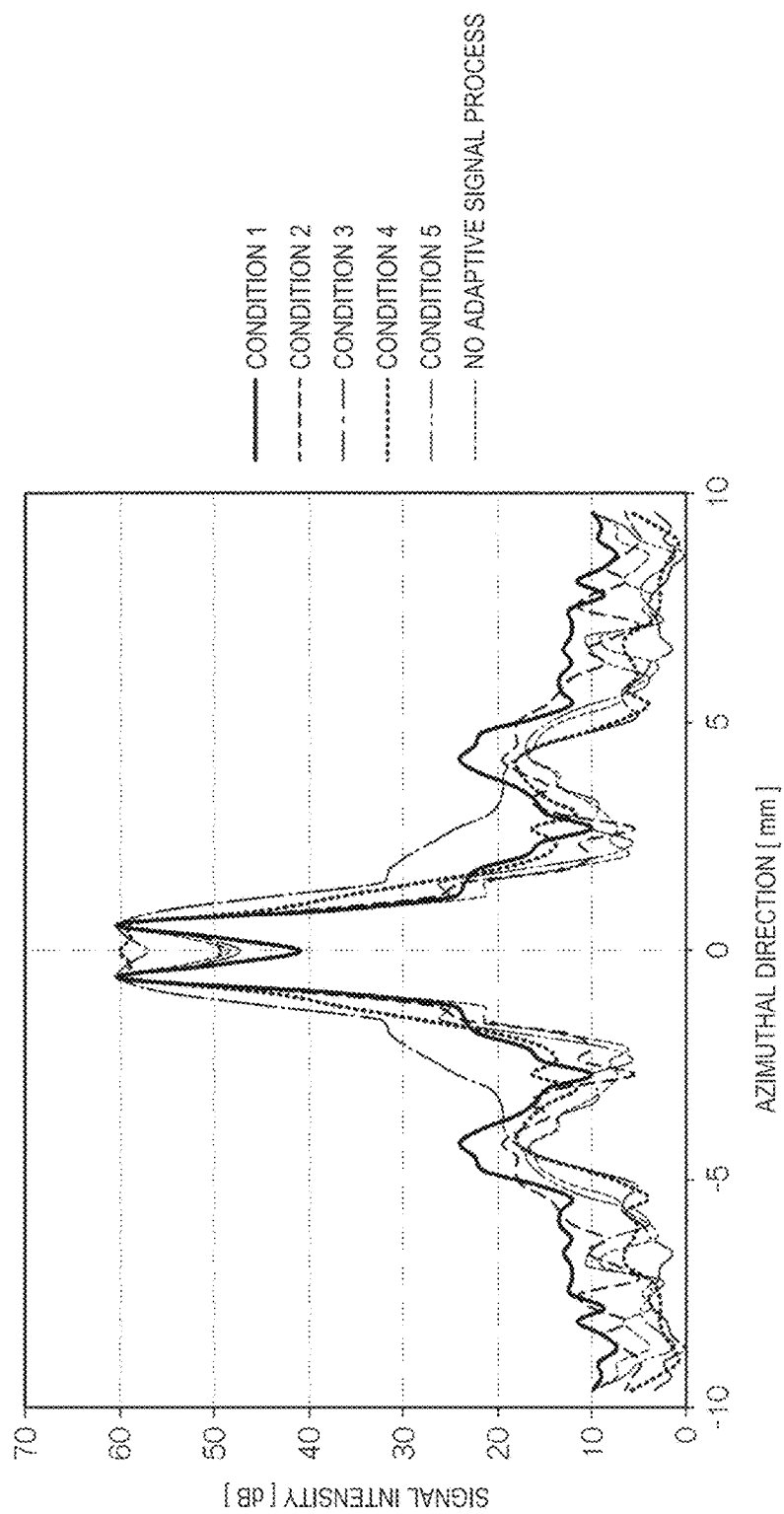
FIG. 11 is a graph illustrating a signal intensity distribution as a result of simulation.
Figure 13:
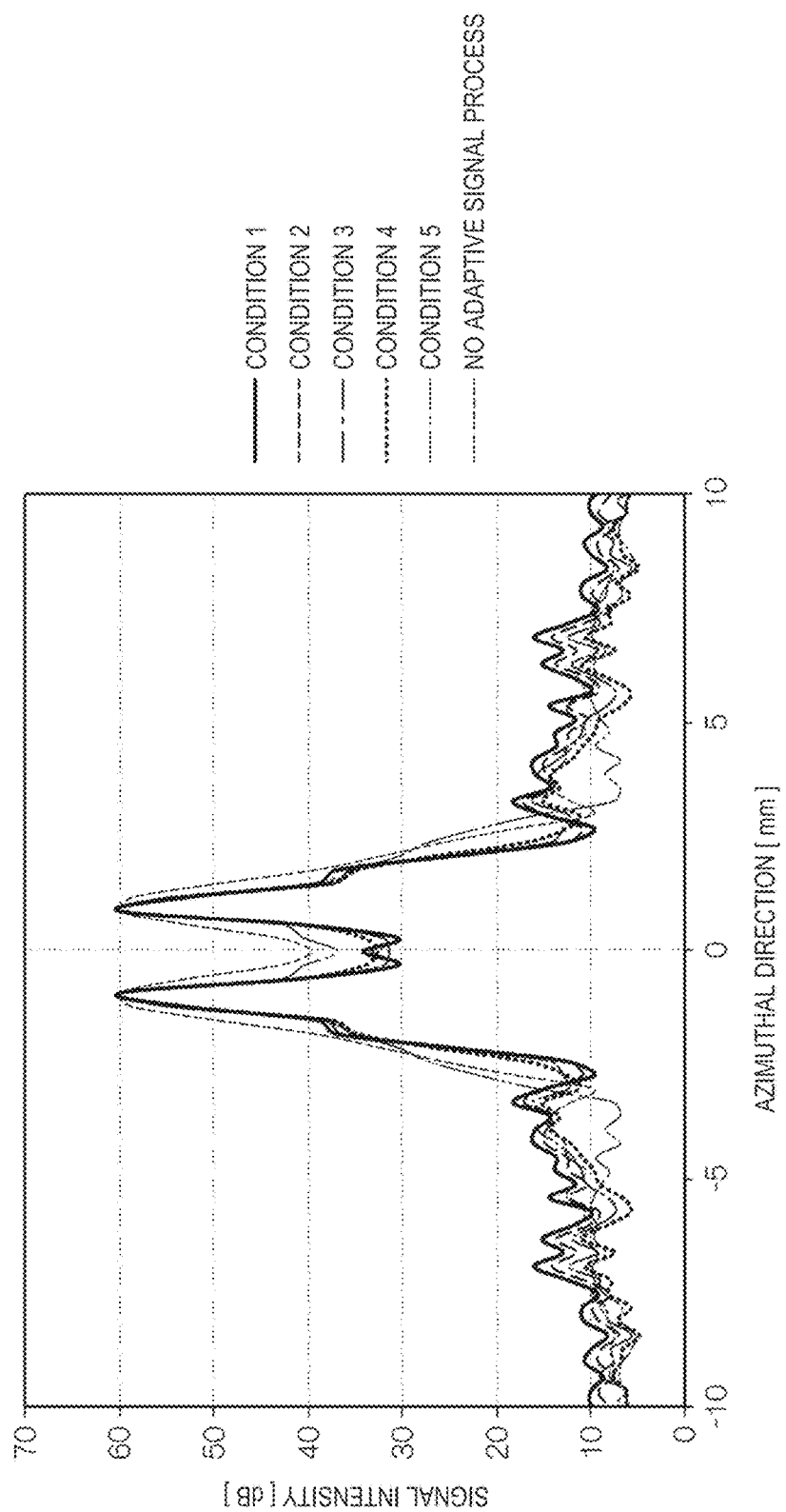
FIG. 13 is a graph illustrating a signal intensity distribution as a result of simulation.

The inventor has verified the effectiveness of the present embodiment. Computer simulation was performed for the verification. A simulation model SM was built for the computer simulation. In the simulation model SM, 64 (M) conversion elements 22 formed a column. A transmission frequency was set to 3.5 MHz. A drive aperture was set to 19.2 mm. In the first transmission mode, the number of transmissions and receptions was set to 64 (S1=1). As illustrated in FIG. 9, the conversion elements 22 were brought into pressing contact with a surface of a target object 71. Two wire phantoms 72 were disposed at a depth of 30 mm from the surface of the target object 71. The wire phantoms 72 were arranged in parallel to the surface of the target object 71. A gap of 1 mm was set between the wire phantoms 72. In Condition 1, adaptive beamforming was performed on each first image signal. A minimum variance (MV) method was used for the adaptive beamforming. In other words, the number L of signals was set to 1 at the number N of groups=64. In Condition 2, the number L of signals was set to 2 at the number N of groups=32. In Condition 3, the number L of signals was set to 4 at the number N of groups=16. In Condition 4, the number L of signals was set to 8 at the number N of groups=8. In Condition 5, the number L of signals was set to 16 at the number N of groups=4. In a comparative example, synthesis using adaptive beamforming was omitted. An image was generated on the basis of various conditions and the simulation model SM.

As illustrated in FIGS. 10A to 10F and FIG. 11, in Conditions 1 to 5, an effect of the adaptive beamforming was confirmed compared with the comparative example. In Conditions 1 to 4, separation of the two wire phantoms 72 was confirmed. In Condition 2, a calculation scale is reduced to $\frac{1}{8}$ of that in Condition 1. In Condition 3, a calculation scale is reduced to $\frac{1}{16}$ of that in Condition 1. Similarly, in Condition 4, a calculation scale is reduced to $\frac{1}{512}$ of that in Condition 1, and, in Condition 5, a calculation scale is reduced to $\frac{1}{4096}$ of that in Condition 1.

Next, the inventor has verified the third transmission mode. A column was formed of 128 conversion elements 22.

A transmission frequency was set to 3.5 MHz. A drive aperture was set to 38.4 mm. The number of transmissions and receptions was set to 64 (K=64). A scanning angle was set to ±22.5 degrees. In the same manner as in FIG. 9, the conversion elements 22 were brought into pressing contact with the surface of the target object 71. An image was generated on the basis of the simulation model SM in Conditions 1 to 5.

As illustrated in FIGS. 12A to 12F and FIG. 13, in Conditions 1 to 5, an effect of the adaptive beamforming was also confirmed compared with the comparative example in a case of a planar wave. In Conditions 1 to 4, separation of the two wire phantoms 72 was confirmed. In Condition 2, a calculation scale is reduced to ⅛ of that in Condition 1. In Condition 3, a calculation scale is reduced to 1/16 of that in Condition 1. Similarly, in Condition 4, a calculation scale is reduced to 1/512 of that in Condition 1, and, in Condition 5, a calculation scale is reduced to 1/4096 of that in Condition 1.

Although the present embodiment has been described in detail, it can be easily understood by a person skilled in the art that various modifications may occur without substantially departing from the novel matters and effects of the invention. Therefore, such modification examples are all intended to be included in the scope of the invention. For example, in the specification or the drawings, a terminology which is described at least once along with another terminology which has a broader meaning or the same meaning may be replaced with another terminology in any location of the specification or the drawings. Configurations and operations of the ultrasonic device unit DV, the ultrasonic device 17, the conversion element 22, and the like are not limited to those described in the present embodiment and may be variously modified. At least the beamforming processor 57 may be formed of, for example, a central processing unit (CPU). In this case, each functional block of the CPU may be realized through a calculation process in software. Instead of the MV method, a multiple signal classification (MUSIC) method, an amplitude and phase estimation (APES) method, an estimation of signal parameters via rotational invariance techniques (ESPRIT) method, or a maximum entropy method (MEM) may be used for the adaptive beamforming.

The entire disclosure of Japanese Patent Application No. 2015-215649 filed on Nov. 2, 2015 is expressly incorporated by reference herein.

What is claimed is:

1. A control device for an ultrasonic image apparatus comprising a processor configured to:
   perform aperture synthesis of output signals from groups of conversion elements which are arranged in a matrix;
   set a number of transmissions of ultrasonic waves based on a transmission mode;
   convert the ultrasonic waves into electric signals;
   sequentially output a first image signal for each of the transmissions;
   output a second image signal for each group by adding the first image signals for that group, while limiting a number of first image signals for each group based on a number of groups and the number of transmissions;
   calculate an adaptive weight based on each second image signal; and
   synthesize the second image signals with each other.

2. The control device for an ultrasonic image apparatus according to claim 1, further comprising:
   transmitter that outputs a transmission signal to a conversion element selected from the groups.

3. The control device for an ultrasonic image apparatus according to claim 2,
   wherein, in a case where the transmission signal defines K output patterns forming a planar wave, a spread wave, or a converged wave in the groups, the number L of first image signals is specified for each group according to the number K of transmissions and the number N of groups based on the following equation:

$$L = \left\lceil \frac{K}{N} \right\rceil \text{ or } \left\lfloor \frac{K}{N} \right\rfloor$$

provided that $$K = \left\lceil \frac{K}{N} \right\rceil \times K \bmod N + \left\lfloor \frac{K}{N} \right\rfloor \times (N - K \bmod N).$$

4. An ultrasonic image apparatus comprising:
   an apparatus main body that includes the control device for an ultrasonic image apparatus according to claim 3; and
   a probe that is connected to the apparatus main body and supports the groups.

5. An ultrasonic image apparatus comprising:
   an apparatus main body that includes the control device for an ultrasonic image apparatus according to claim 2; and
   a probe that is connected to the apparatus main body and supports the groups.

6. The control device for an ultrasonic image apparatus according to claim 1,
   wherein, when S1 conversion elements which do not overlap each other among M conversion elements forming a column are sequentially driven, the number L of first image signals is specified for each group according to the number K of transmissions and the number N of groups based on the following equations:

$$K = \frac{M}{S1}$$
$$L = \left\lceil \frac{K}{N} \right\rceil \text{ or } \left\lfloor \frac{K}{N} \right\rfloor$$

provided that $$K = \left\lceil \frac{K}{N} \right\rceil \times K \bmod N + \left\lfloor \frac{K}{N} \right\rfloor \times (N - K \bmod N).$$

7. An ultrasonic image apparatus comprising:
   an apparatus main body that includes the control device for an ultrasonic image apparatus according to claim 6; and
   a probe that is connected to the apparatus main body and supports the groups.

8. The control device for an ultrasonic image apparatus according to claim 1,
   wherein, when S1 conversion elements which are deviated by S2 among M conversion elements forming a column are sequentially driven, the number L of first image signals is specified for each group according to the number K of transmissions and the number N of groups based on the following equations:

$$K = \frac{M - S2}{S1 - S2}$$

$$L = \left\lceil \frac{K}{N} \right\rceil \text{ or } \left\lfloor \frac{K}{N} \right\rfloor$$

provided that $$K = \left\lceil \frac{K}{N} \right\rceil \times K \bmod N + \left\lfloor \frac{K}{N} \right\rfloor \times (N - K \bmod N).$$

9. An ultrasonic image apparatus comprising:
an apparatus main body that includes the control device for an ultrasonic image apparatus according to claim 8; and
a probe that is connected to the apparatus main body and supports the groups.

10. The control device for an ultrasonic image apparatus according to claim 1,
wherein the number of groups is two or larger.

11. An ultrasonic image apparatus comprising:
an apparatus main body that includes the control device for an ultrasonic image apparatus according to claim 10; and
a probe that is connected to the apparatus main body and supports the groups.

12. The control device for an ultrasonic image apparatus according to claim 1, further comprising:
an input that is connected to an input device and inputs the number of groups.

13. An ultrasonic image apparatus comprising:
an apparatus main body that includes the control device for an ultrasonic image apparatus according to claim 12; and
a probe that is connected to the apparatus main body and supports the groups.

14. The control device for an ultrasonic image apparatus according to claim 1, further comprising:
a setter that sets the number of groups based on an input value for specifying a resolution of the second image signal.

15. An ultrasonic image apparatus comprising:
an apparatus main body that includes the control device for an ultrasonic image apparatus according to claim 14; and
a probe that is connected to the apparatus main body and supports the groups.

16. The control device for an ultrasonic image apparatus according to claim 1,
wherein the processor is further configured to add values of the first image signals together for each of a plurality of coordinate points.

17. An ultrasonic image apparatus comprising:
an apparatus main body that includes the control device for an ultrasonic image apparatus according to claim 1; and
a probe that is connected to the apparatus main body and supports the groups.

18. An ultrasonic image forming method comprising:
performing aperture synthesis of output signals from groups of conversion elements which are arranged in a matrix;
setting a number of transmissions of ultrasonic waves based on a transmission mode;
converting the ultrasonic waves into electric signals;
sequentially outputting a first image signal for each of the transmissions;
outputting a second image signal for each group by adding the first image signals for that group, while limiting a number of first image signals for each group based on a number of groups and the number of transmissions;
calculating an adaptive weight based on each second image signal; and
synthesizing the second image signals with each other.

* * * * *